US00PP28595P3

(12) United States Plant Patent

Walsh et al.

(10) Patent No.: US PP28,595 P3

(45) Date of Patent: Nov. 7, 2017

(54) APPLE TREE NAMED 'CP 101'

(50) Latin Name: ***Malus domestica* Borkh**
Varietal Denomination: CP 101

(71) Applicant: UNIVERSITY OF MARYLAND, College Park, MD (US)

(72) Inventors: Christopher S. Walsh, University Park, MD (US); Julia M. Harshman, Owings, MD (US)

(73) Assignee: University of Maryland, College Park, MD (US)

( * ) Notice: Subject to any disclaimer, the term of this patent is extended or adjusted under 35 U.S.C. 154(b) by 240 days.

(21) Appl. No.: 14/544,045

(22) Filed: Nov. 20, 2014

(65) Prior Publication Data

US 2015/0150167 P1 May 28, 2015

Related U.S. Application Data

(60) Provisional application No. 61/963,085, filed on Nov. 22, 2013.

(51) Int. Cl.
*A01H 5/08* (2006.01)

(52) U.S. Cl.
USPC ..... Plt./161

(58) Field of Classification Search
USPC ..... Plt./161
CPC ..... A01H 5/0875
See application file for complete search history.

(56) References Cited

U.S. PATENT DOCUMENTS

PP7,880 P 6/1992 Cripps

*Primary Examiner* — Kent L Bell

(74) *Attorney, Agent, or Firm* — Rosenberg, Klein & Lee

(57) ABSTRACT

A new and distinctive variety of *Malus domestica* apple tree, named 'CP 101' that is distinguished by its attractive fruit color and flavor, early harvest season that is different than its seed parent, and its moderate scion dwarfing.

8 Drawing Sheets

Figure 1:
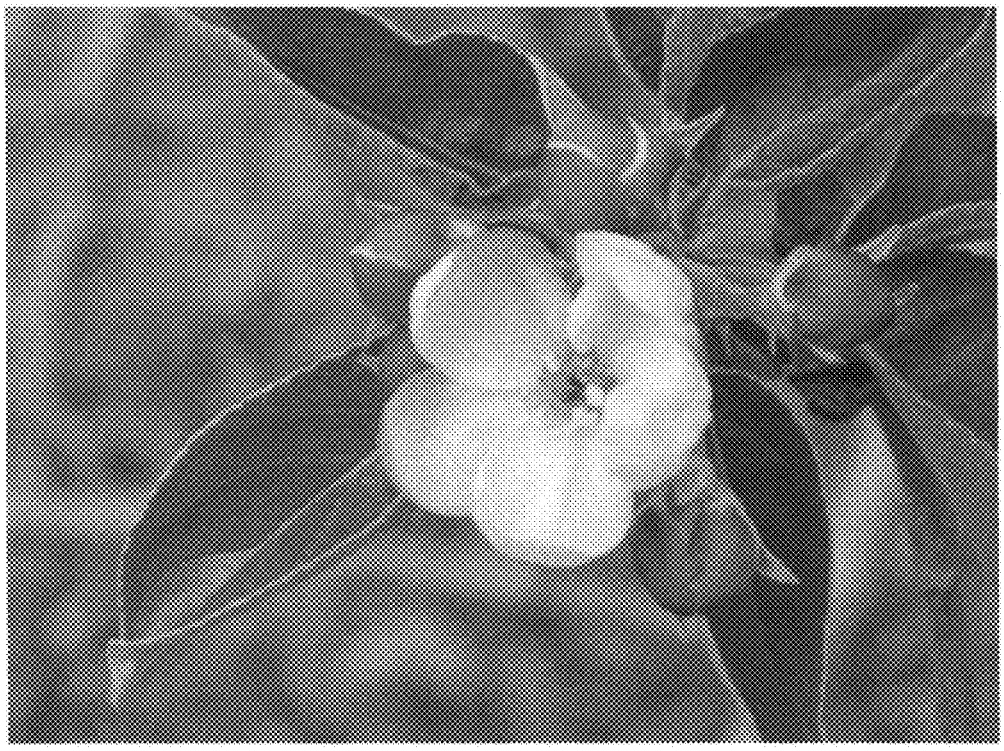

Latin name: *Malus domestica* Borkh.
Varietal denomination: 'CP 101'.

BACKGROUND OF THE INVENTION

The new variety of apple tree 'CP 101' was created in the course of a planned breeding program carried out at in Keedysville, Md. 'CP 101' originated as an open-pollinated seed of 'Cripps Pink' (U.S. Plant Pat. No. 7,880, seed parent) and an unknown 'CGM' seedling (not patented, pollen parent). 'CGM' seedlings were the result of an open-pollinated cross between seedlings of 'McIntosh Wijcik' (not patented, seed parent) and 'Gala' (not patented, pollen parent) generated by the inventors in Keedysville, Md. The plantings were isolated from other plantings, so while they were the result of open-pollination, the authors are fairly certain of the pollen parentage. 'Cripps Pink', 'CGM', 'McIntosh Wijcik' and 'Gala' were all cultivated between the years 1991 and 1999. CGM seedlings were on their own roots, while the varieties 'Cripps Pink', 'McIntosh Wijcik' and 'Gala' were grafted on M.7. 'CP 101' was selected as a single plant from among a population of seedlings derived from these parents for its precocity, productivity, tree architecture, attractive fruit color and flavor, and adaptation to the hot, wet summer growing conditions present in the Mid-Atlantic region of the United States. It is distinguished from its seed parent by its early harvest season which in Keedysville, Md. is the first week of October. 'Cripps Pink' is harvested at that same location three to four weeks later. In the tenth leaf, the height and spread of the original self-rooted 'CP 101' seedling was 3.02 m and 3.27 m, respectively. Wild-type 'Cripps Pink' seedlings at the same age measured 4.14 m and 4.57 m, respectively. From this we estimate a minimum of 30% scion dwarfing. 'CP 101' is a departure from other dwarfing, tree architecture releases in that it is neither a single-leader, columnar type (ie. 'Maypole', 'Tuscan', 'Hercules', 'Moonlight', 'Trajan', or 'Telamon', to name a few) nor is it a spur type tree characterized by the very short internode length (ie. 'Spur-type Red Delicious', 'Early Spur Rome', 'Cumberland Spur', 'Oregon Spur', etc). 'CP 101' retains an attractive "Christmas tree" shape, while being 30% smaller than wild-type counterparts. Internodes are somewhat reduced, but not generally comparable to traditional spur types.

Table 1 represents fruit quality indices of 'CP 101', 'Granny Smtih', and 'Pink Lady' varieties. In Table 1, pressure is a measure of fruit firmness, SSC is a measure of soluble solid content of fruit in units ° Brix, and SPI is a measure of the starch pattern index on the Cornell 8-point starch chart. The varieties were sampled on Nov. 5, 2014 and data is presented as an average of twenty fruit.

TABLE 1

| | Firmness (kilo) | SSC | Starch | Fruit Weigh (g) |
|---|---|---|---|---|
| 'CP 101 | 7.86 | 16.2 | 7 | 153.4 |
| 'Granny Smith' | 7.03 | 12.05 | 6.5 | 178.25 |
| 'Pink Lady' | 8.6 | 16.7 | 5 | 158.8 |

Important features of 'CP 101' with respect to prior art cultivars include low-pruning tree architecture, precocity and high producticity with low biennial bearing, and improved fruit quality and pleasing aesthetic appearance. 'CP 101' is adapted to Mid-Atlantic, U.S.A. growing conditions.

Asexual propagation by budding was first carried out in Cecilton, Md. The variety is compatible with 'Budagovski 9' and 'Merton-Malling 111' rootstocks, which is currently the industry standard. Successful grafting of budwood onto Merton-Malling 111 rootstocks was accomplished. This is the first in a series of second-generation trees we have developed with size control and tree-architecture benefits conferred by the scion. These make it applicable to intensive apple management systems.

BRIEF DESCRIPTION OF THE PHOTOGRAPHS

Figure 2:
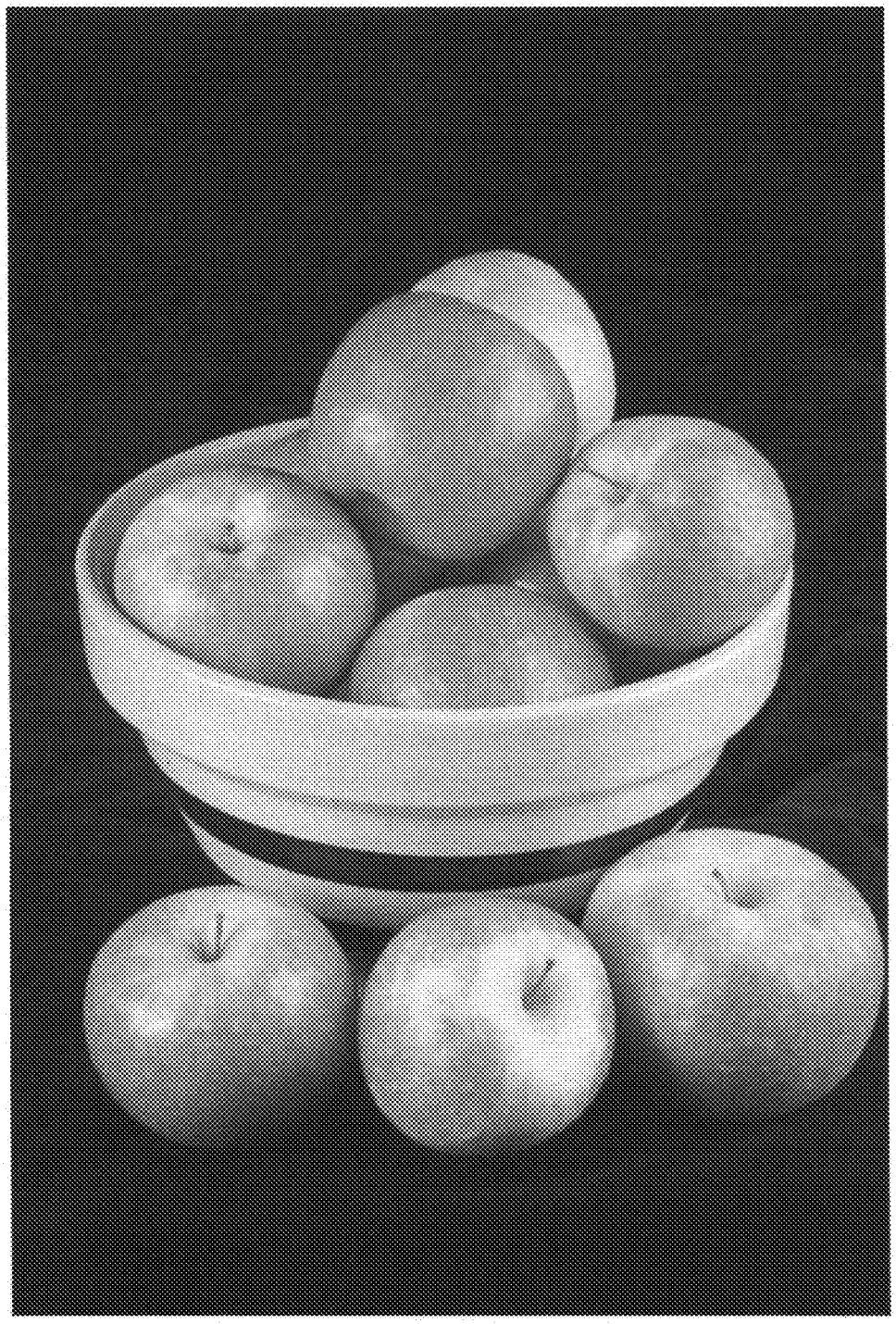
Figure 3:
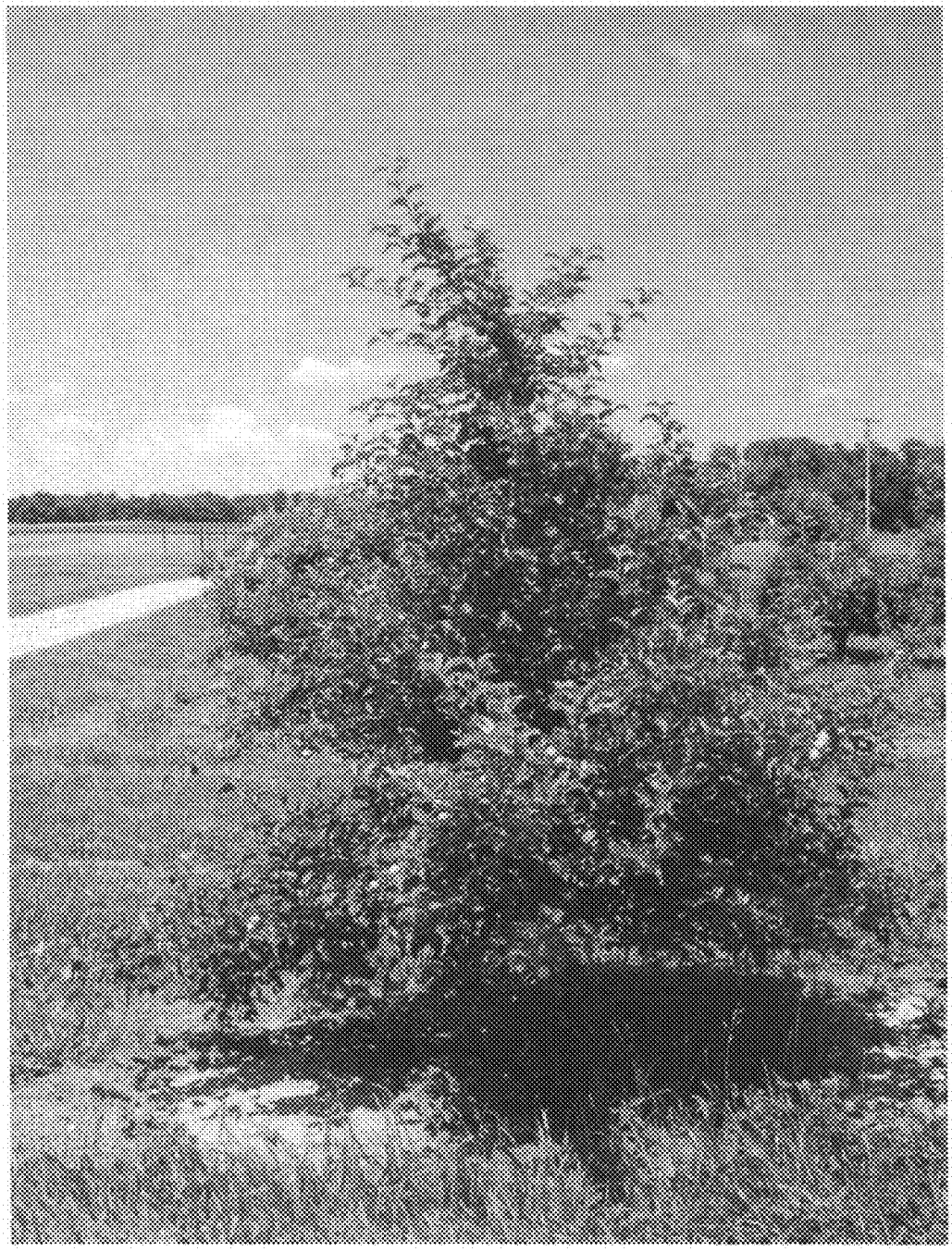
Figure 4:
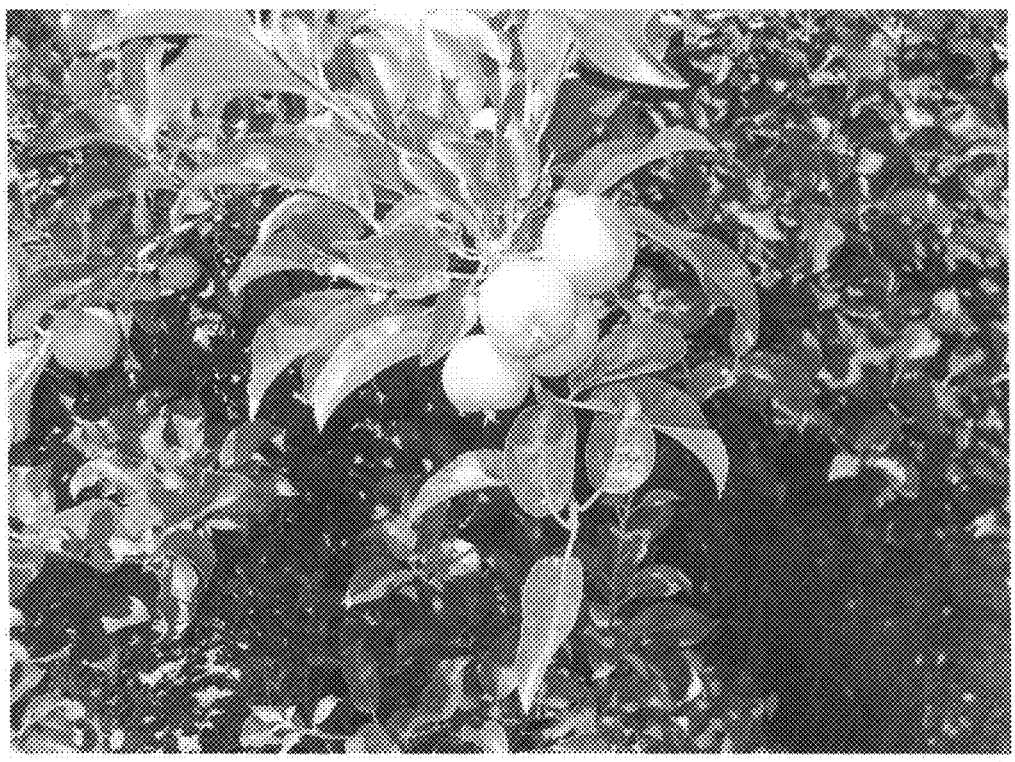
Figure 5:
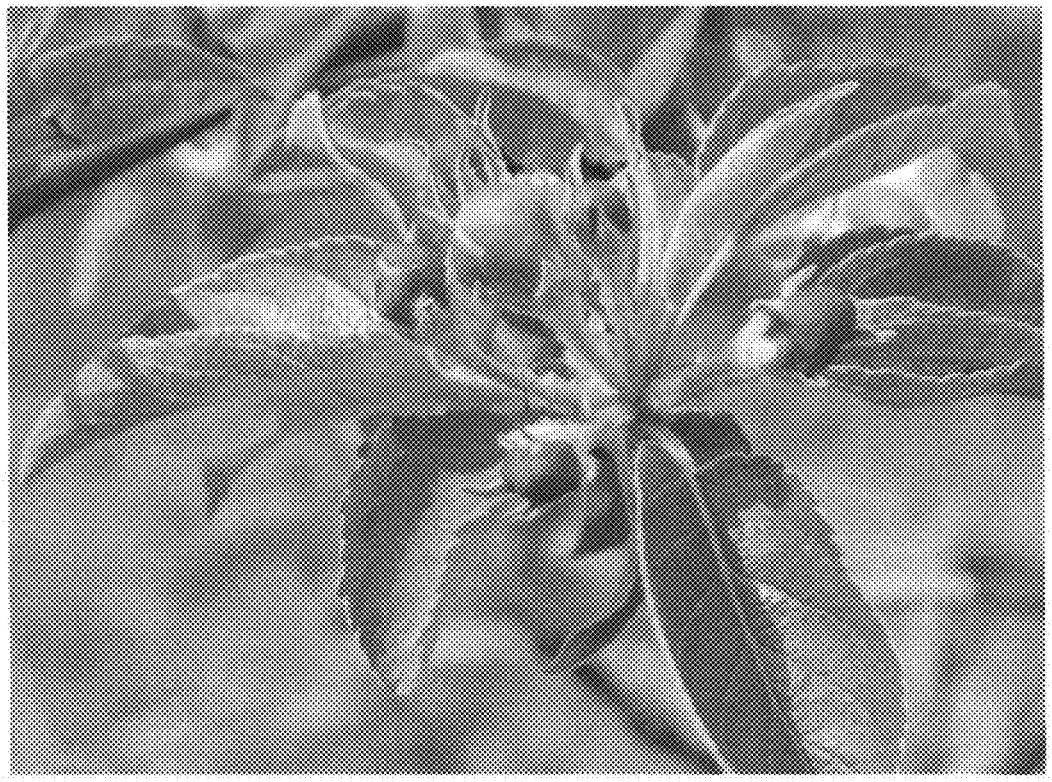
Figure 6:
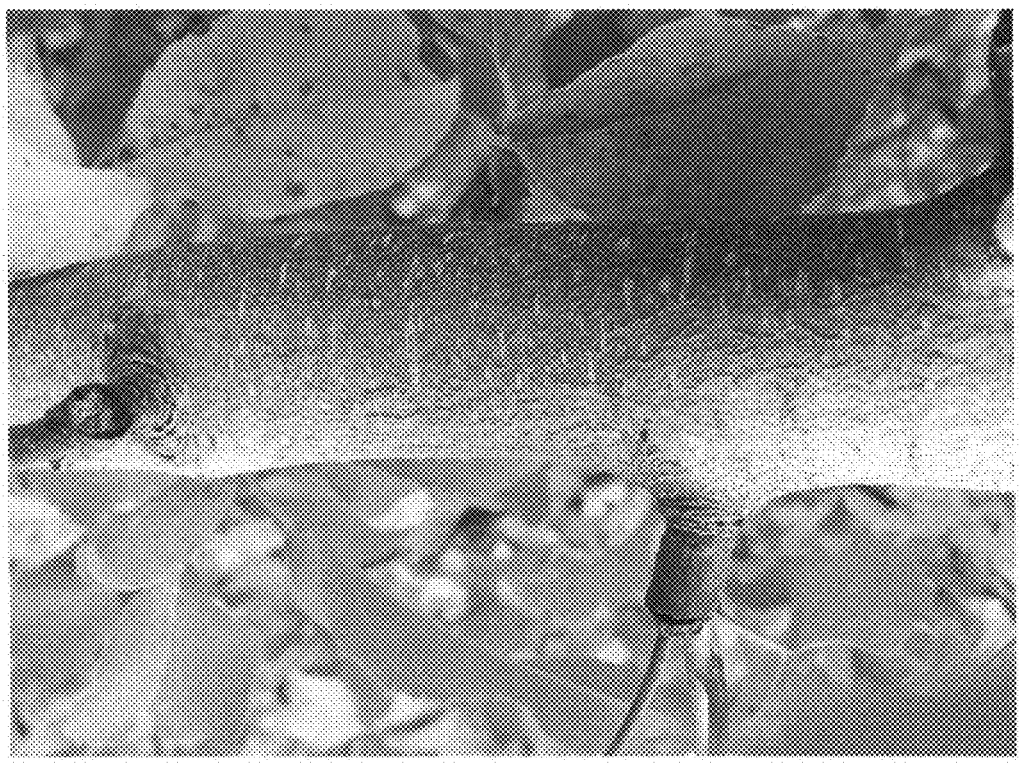
Figure 7:
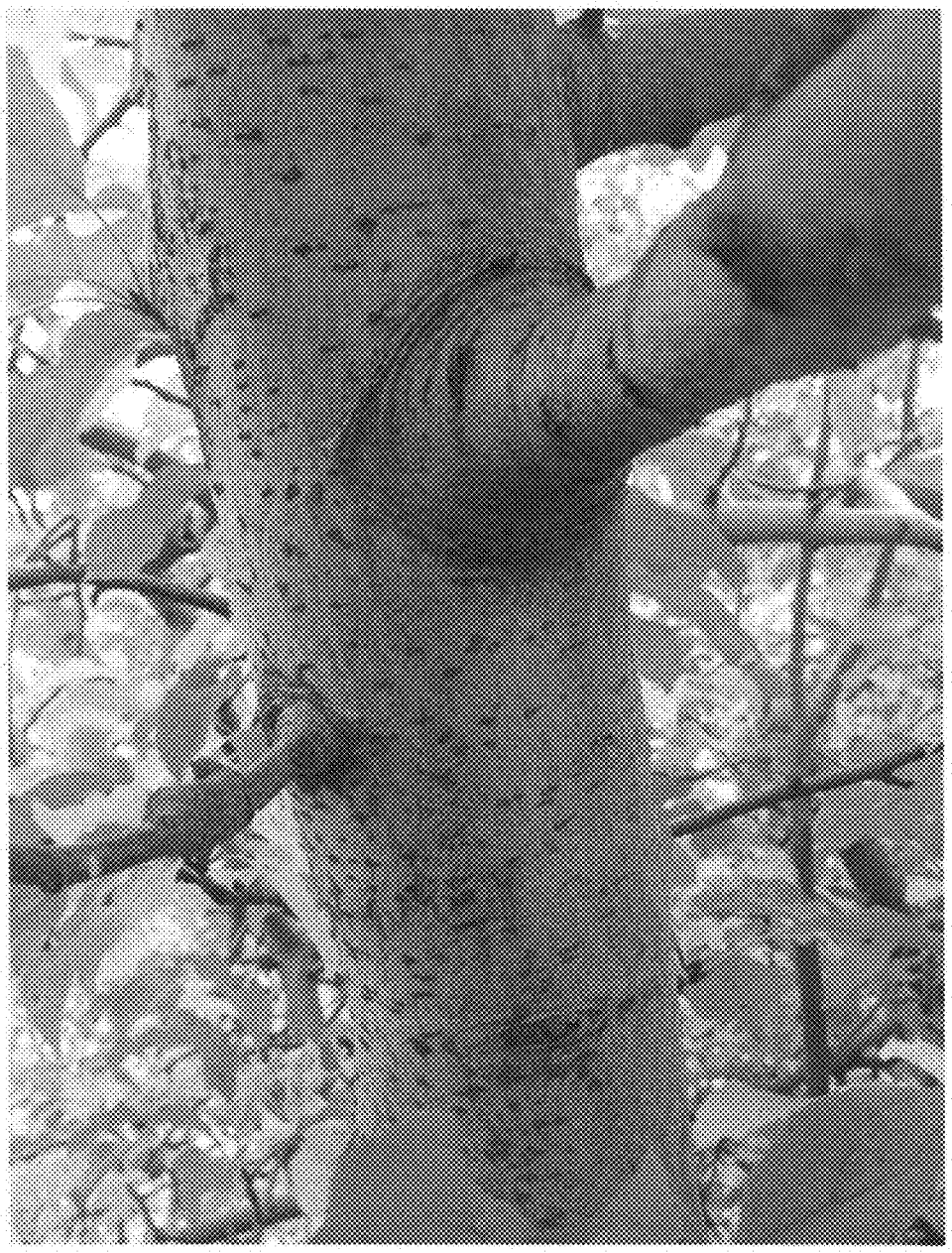
Figure 8:
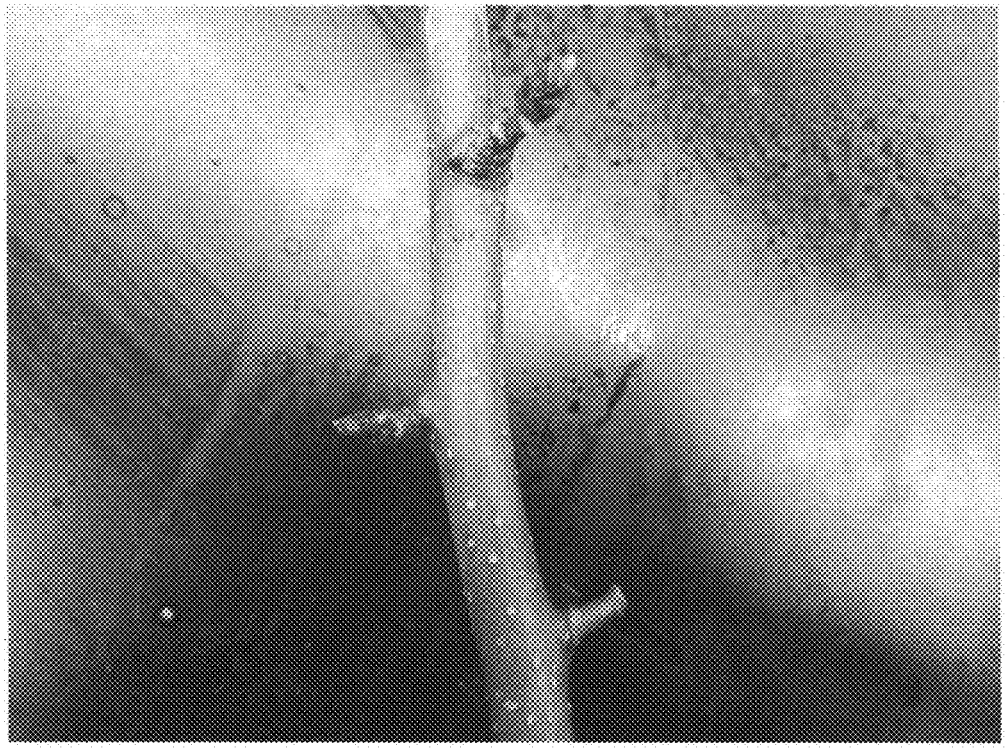

FIG. 1 shows a blossom of 'CP 101'
FIG. 2 shows the fruit of 'CP 101'
FIG. 3 shows the tree architecture of 'CP 101'
FIG. 4 shows the leaves and immature fruit of 'CP 101';
FIG. 5 shows the floral buds of 'CP 101';
FIG. 6 shows the scaffold branch of 'CP 101';
FIG. 7 shows the trunk of 'CP 101' at waist height; and
FIG. 8 shows budwood stick of 'CP 101'.

DETAILED DESCRIPTION OF THE NEW CULTIVAR

The following detailed botanical description is based on observations of the ten year old 'CP 101' apple tree grown at Keedysville, Md. Color descriptions refer to The Royal Horticultural Society Colour Chart, published in 2001. It should be understood that the characteristics described will vary somewhat depending upon cultural practices and climatic conditions, and can vary with location and season. Quantified measurements are expressed as an average of measurements taken from a number of individual fruits of the new variety. The measurements of any individual plant, or any group of plants, of the new variety may vary from the stated average. When multiple colors were observed, the primary color is listed first and the secondary color is listed second.

Tree:

*Vigor*.—Low to Medium vigor.
*Habit*.—Spreading.
*Bearing*.—Spurs and laterals on last year's wood.
*Size*.—Height: 3.02 m; spread: 3.27 m.
*Trunk*.—Diameter 8.7 cm at 30 cm above soil line; bark texture smooth; color grey-brown 199C.
*Trunk lenticels*.—Density 8 per square inch; length 0.1 to 0.2 cm; color grey-brown 199B.
*Branches* (*scaffold limbs located about* 1 *m above ground*).—Length 152 cm; diameter 2.2 cm (near trunk, past collar); crotch angle 90 degree; color greyed-green 197B.
*Branch lenticels*.—Density 6 per square inch; length 0.1 cm; color greyed-green 197D.
*Winter hardiness*.—Hardy in Keedysville, Md., USDA Hardiness Zone 6b (−5° F. to 0° F.).
*Dormant one year old shoot*.—Size. — Diameter 0.25 cm; length 28 cm.
*Color*.—Grey-brown N199C. Internode length. — 3.7 cm.
*Lenticels*.—Density 88 per square inch; length 0.1 cm; color grey-brown N199D.

Flowers:

*Bud*.—Quantity per spur 5 to 6; length 1.3 cm; diameter 0.7 cm; color red-purple 64C with white N155C.
*Petals*.—Quantity per flower 5; cupped upwards, free, not touching; width 0.9 cm; length 1.6 cm; both the upper (adaxial) surface and lower (abaxial) surface of the petals are the same color, namely, white NN155B and red-purple 63C when fully open. The petals are obtuse, with an entire margin with some undulation. The petal terminates into a 2 mm long, 0.9 mm wide base, which is a petiole-like structure that attaches to the floral tube.
*Flower*.—The blossom (or flower cluster) consists of five, sometimes six, individual flowers. The diameter of the blossom is typically 7.6 cm with a height of 4.5 cm measured from the uppermost bud scale scar. Individual flowers in the flower cluster measure 4.1 cm in height and between 3.9 cm-4.4 cm in diameter.
*Pistil*.—Individual flowers have a single fused pistil which divides into five distinct styles. The pistil length is 7.9 mm. The pistil separates into five individual styles at 3.8 mm above the point of attachment of the pistil to the hypanthium. Pistil diameter at the base is 1.1 mm and the pistil color is 144D as measured using The Royal Horticultural Colour Chart. The five individual lobes of the pistil are each about 4.1 mm in length, with each of the lobes terminating in a stigmatic surface of 1 mm diameter.
*Sepals*.—Quantity per flower 5; color yellow-green 142B. Sepals are hirstute and lanceolate with a sharp apex. Sepal length is 8 to 9 mm with width ranges from 3 to 4.4 mm at their point of attachment to the hypanthicum.
*Pedicel*.—Length 2.0 cm; diameter 0.1 cm; color yellow-green 144B.
*Anthers*.—Quantity per flower 17; length 1.0 cm; stamen color orange-white 159A; pollen color yellow 4D.
*Stigma*.—Color yellow-green 144D. Style. — Length 0.9; color yellow-green 144C.
*Ovary*.—Length 0.5 cm; width 0.3 cm; color green 143A.
*Time of flowering*.—Early to mid-April in Keedysville, Md., similar to Gala/Cripps Pink.
*Pollination requirement*.—No special pollination requirements known.

Leaf (first fully expanded):

*Size*.—Length 7.6 cm; width 4.6 cm.
*Margin*.—Crenate.
*Surface texture*.—Upper surface medium glossy; Lower surface weak pubescent. Color. — Upper surface green 143A; lower surface yellow-green 144B.
*Shape*.—Ovate; apex acuminate; base equilateral.
*Petiole*.—Length 3.2 cm; width 0.2 cm; color yellow-green 144B.

Fruit:

*Quantity*.—Typically, one fruit is borne per cluster, although this can range to as many as three fruit when there is a heavy crop and no thinning treatments are applied.
*Size*.—Diameter 7.0 cm; height 5.7 cm.
*Fruit shape*.—Oblate to Conic. Position of maximum diameter. — Equator.

*Ribbing*.—Absent.
*Crowning at calyx end*.—Absent.
*Aperture of eye*.—Open.
*Depth of eye basin*.—Medium, 1 cm.
*Width of eye basin*.—Medium, 2.0 cm.
*Lenticels*.—Medium, diameter 0.7 mm; Density 6 per cm.
*Locule*.—Aperture of locule in transverse section is closed; Average size of locule is 7.2 mm by 4.3 mm. There are five locules per fruit.
*Stalk*.—Diameter 0.5 cm; length 1.5 cm; color greyed-orange 167C.
*Depth of stalk cavity*.—Medium, 1.5 cm.
*Width of stalk cavity*.—Medium, 2.0 cm.
*Size of lenticels*.—Small, 1 mm.
*Bloom of skin*.—Absent.
*Greasiness of skin*.—Absent.
*Ground color of skin*.—Green-Yellow 1C.
*Over color of skin*.—Red 53B stripe with red 47C blush over approximately 90% of surface.
*Flesh*.—Texture crisp; medium juiciness; color yellow-white 158C.
*Seeds*.—Quantity per fruit 5; teardrop shape; length 0.7 cm, width 0.5 cm; color brown 200D.
*Aroma*.—Weak.
*Harvest date*.—October 15, 3 to 4 weeks before 'Cripps Pink' (U.S. Plant Pat. No. 7,880).
*Storage*.—Fruit remains in good condition after 70 days in storage at 4±0.5° C.
*Disease/pest resistance*.—fruit showed better than average tolerance to Brown Marmorated Stink Bug; fruit were susceptible to bitter rot (*Glomerella cingulata*) in years conducive to the disease; tree showed some field tolerance to fire blight (*Erwinia amylovora* (Burrill 1882) Winslow et al. 1920) following bloom infection and hail storms.
*Market use*.—Dessert. 'CP 101' apples are firm and flavorful. Taste tests have shown them to have the balance of sweetness and acidity favored by fresh-market apple consumers.

What is claimed is:

1. A new and distinct Apple tree known as 'CP 101' as described and illustrated herein.

* * * * *